United States Patent
Picha et al.

[11] Patent Number: 6,071,310
[45] Date of Patent: Jun. 6, 2000

[54] SPINAL IMPLANT

[75] Inventors: George J. Picha, 6654 Beachwood Dr., Independence, Ohio 44131; Jeffrey A. Goldstein, New York, N.Y.

[73] Assignee: George J. Picha, Independence, Ohio

[21] Appl. No.: 09/197,819

[22] Filed: Nov. 23, 1998

Related U.S. Application Data

[63] Continuation of application No. 08/859,577, May 20, 1997, Pat. No. 5,876,457.

[51] Int. Cl.⁷ ........................................................ A61F 2/44
[52] U.S. Cl. .................................................. 623/17; 606/61
[58] Field of Search ................................ 623/17; 606/61, 606/73, 60, 62, 72

[56] References Cited

U.S. PATENT DOCUMENTS

| | | |
|---|---|---|
| D. 377,095 | 12/1996 | Michelson . |
| D. 377,096 | 12/1996 | Michelson . |
| 4,017,571 | 4/1977 | Rice et al. . |
| 4,272,855 | 6/1981 | Frey . |
| 4,385,405 | 5/1983 | Teinturier . |
| 4,608,052 | 8/1986 | Van Kampen et al. . |
| 4,673,409 | 6/1987 | Van Kampen . |
| 4,772,287 | 9/1988 | Ray et al. . |
| 4,828,563 | 5/1989 | Muller-Lierheim . |
| 4,834,757 | 5/1989 | Brantigan . |
| 4,846,834 | 7/1989 | von Recum et al. . |
| 4,865,603 | 9/1989 | Noiles . |
| 4,904,260 | 2/1990 | Ray et al. . |
| 4,955,907 | 9/1990 | Ledergerber . |
| 4,961,740 | 10/1990 | Ray . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,158,571 | 10/1992 | Picha . |
| 5,180,381 | 1/1993 | Aust et al. . |
| 5,207,709 | 5/1993 | Picha . |
| 5,236,453 | 8/1993 | Picha . |
| 5,263,953 | 11/1993 | Bagby . |
| 5,306,307 | 4/1994 | Senter et al. . |
| 5,306,308 | 4/1994 | Gross et al. . |
| 5,306,309 | 4/1994 | Wagner et al. . |
| 5,330,473 | 7/1994 | Howland . |
| 5,445,639 | 8/1995 | Kuslich et al. . |
| 5,458,638 | 10/1995 | Kuslich et al. . |
| 5,484,437 | 1/1996 | Michelson . |
| 5,489,307 | 2/1996 | Kuslich et al. . |
| 5,489,308 | 2/1996 | Kuslich et al. . |
| 5,496,318 | 3/1996 | Howland et al. . |
| 5,505,732 | 4/1996 | Michelson . |
| 5,514,180 | 5/1996 | Heggeness et al. . |
| 5,522,899 | 6/1996 | Michelson . |
| 5,545,164 | 8/1996 | Howland . |
| 5,545,166 | 8/1996 | Howland . |
| 5,593,409 | 1/1997 | Michelson . |
| 5,658,337 | 8/1997 | Kohrs et al. . |
| 5,683,463 | 11/1997 | Godefroy et al. ........................ 623/17 |
| 5,702,391 | 12/1997 | Lin . |
| 5,702,450 | 12/1997 | Bisserie ..................................... 623/17 |
| 5,709,683 | 1/1998 | Bagby ....................................... 623/17 |
| 5,800,547 | 9/1998 | Schafer et al. ............................ 623/17 |
| 5,876,457 | 3/1999 | Picha et al. ............................... 623/17 |

*Primary Examiner*—Bruce Snow
*Attorney, Agent, or Firm*—Pearne, Gordon, McCoy & Granger LLP

[57] ABSTRACT

A spinal implant including a hollow, generally tubular shell having an exterior lateral surface, a leading end, and a trailing end. The shell has a helical thread projecting from its exterior surface. The thread includes a plurality of pillars. Each pillar has a height of 100–4500 microns and a lateral dimension at the widest point of 100–4500 microns. The exterior surface has a plurality of holes therethrough to permit bone growth therethrough. The spinal implant may alternatively have a plurality of pillars projecting from its exterior surface in a regular, non-helical array.

15 Claims, 5 Drawing Sheets

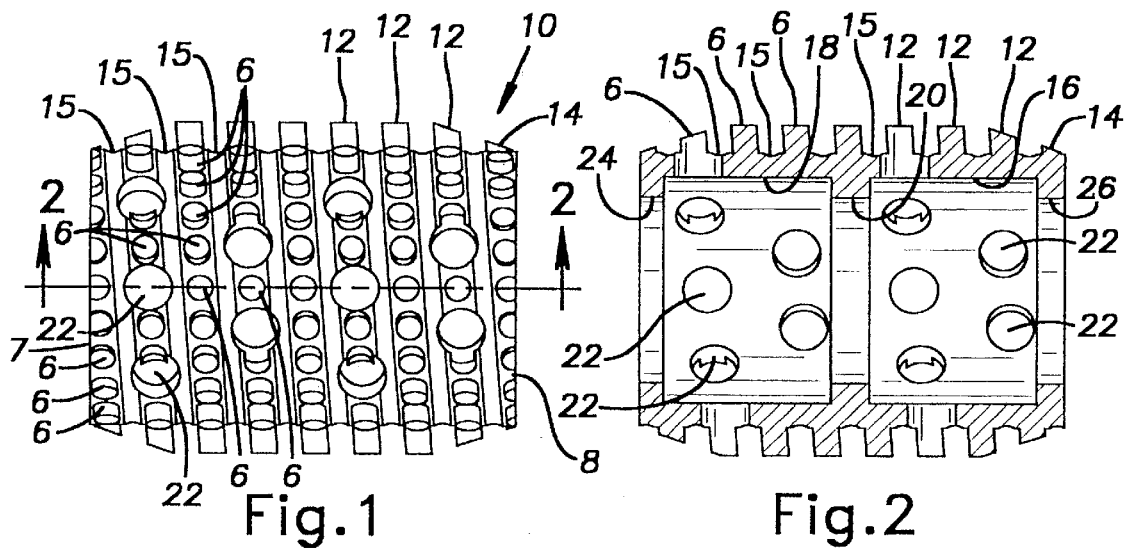
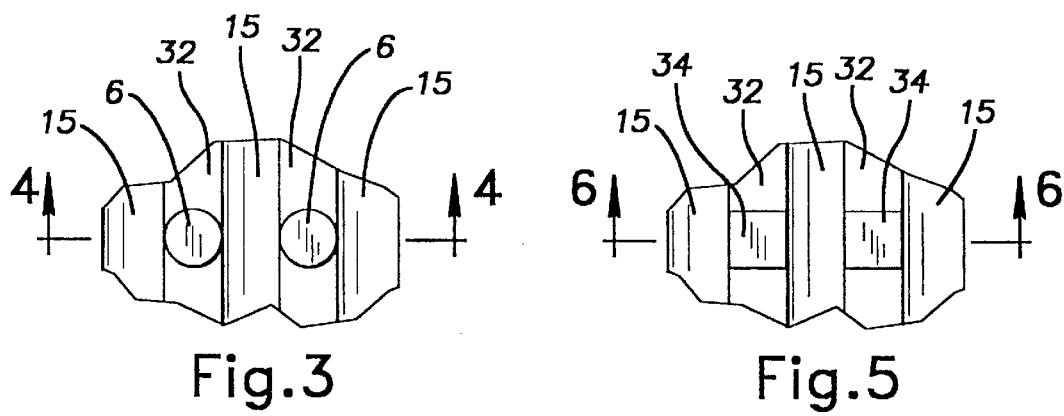
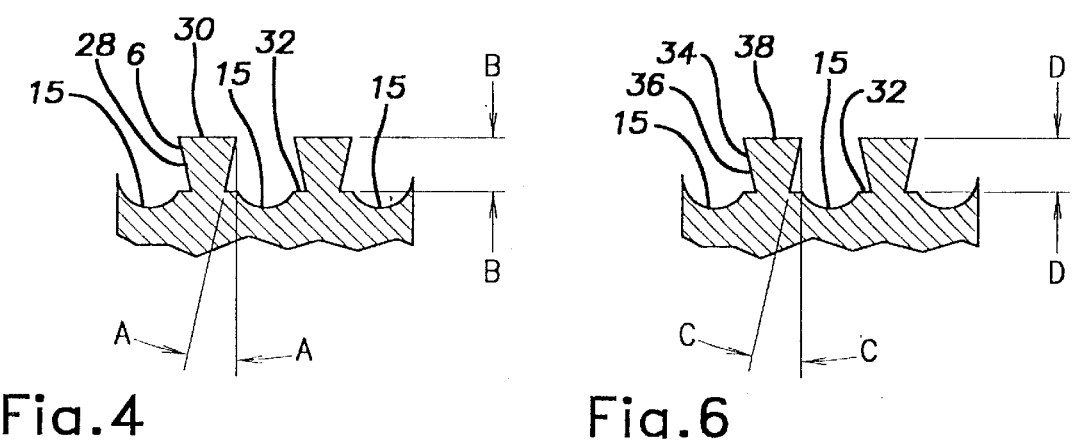

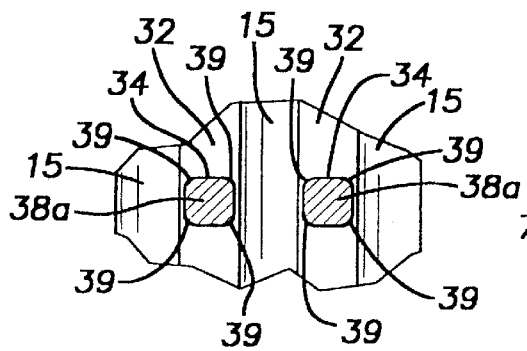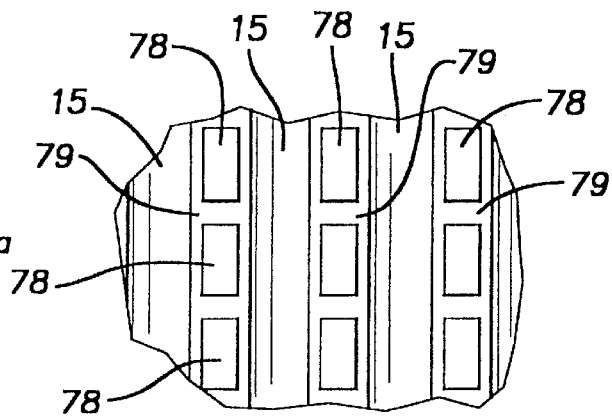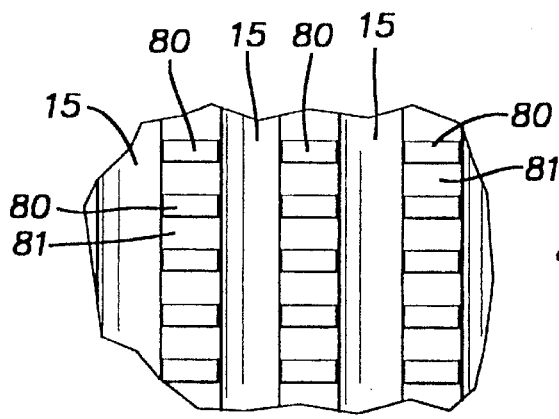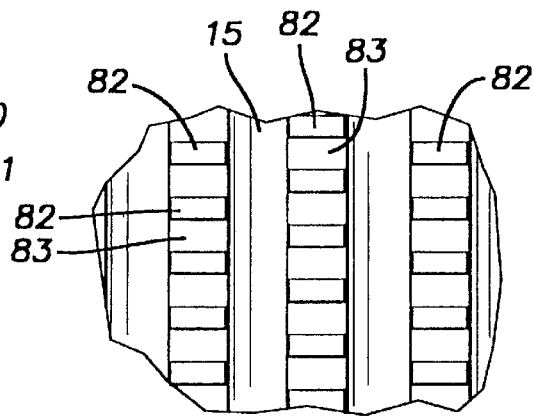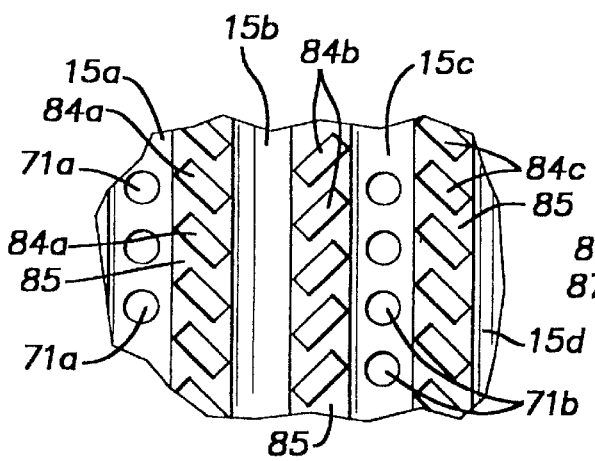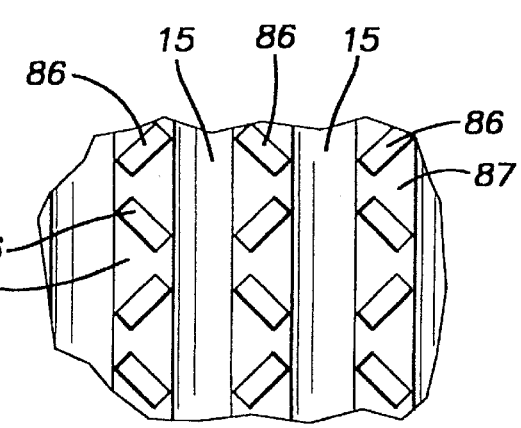

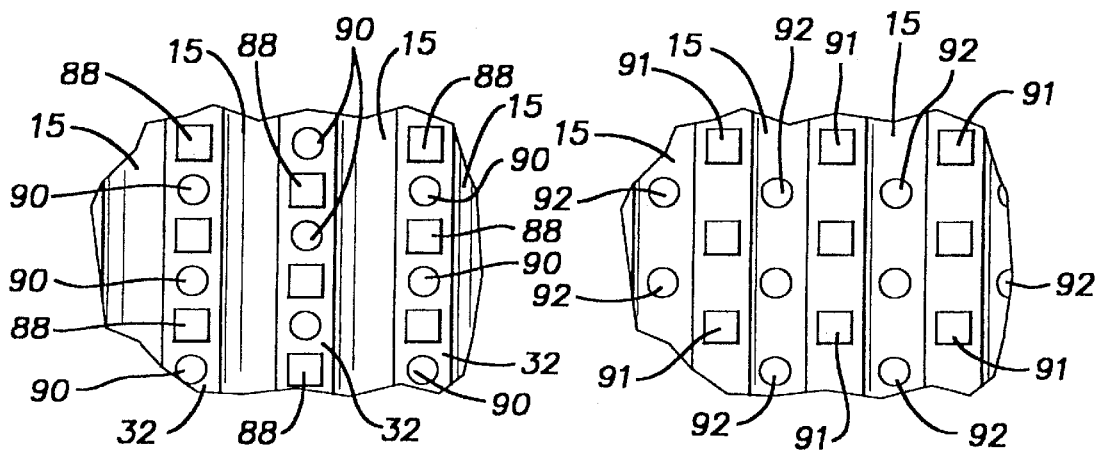
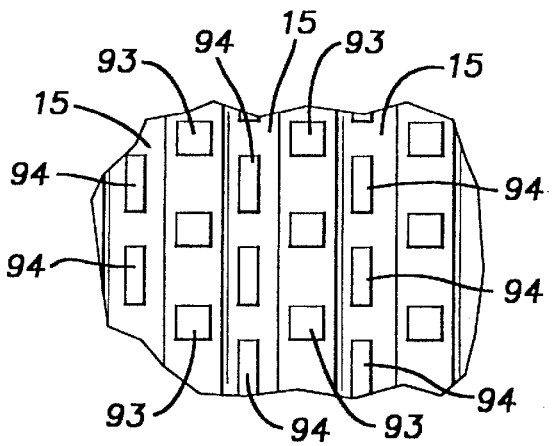
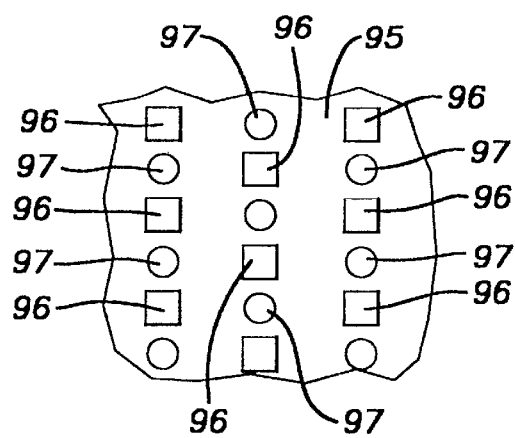
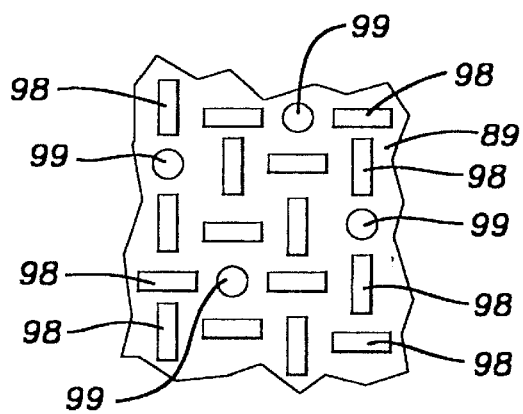
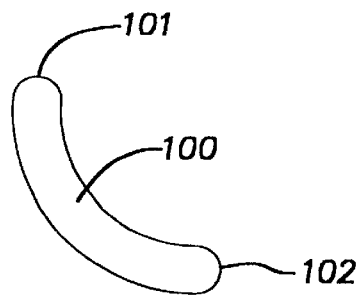

SPINAL IMPLANT

CROSS-REFERENCE TO RELATED APPLICATION

This is a continuation of application Ser. No. 08/859,577, filed May 20, 1997, now U.S. Pat. No. 5,876,457.

BACKGROUND OF THE INVENTION

This invention relates generally to surgical devices for stabilizing the spine, and more particularly to a spinal implant for use in fusing and stabilizing adjoining spinal vertebrae.

Chronic back problems cause pain and disability for a large segment of the population. In many cases, the chronic back problems are attributed to relative movement between vertebrae in the spine. Spinal surgery includes procedures to stabilize adjacent vertebrae. Common stabilization techniques include fusing the vertebrae together.

Fusion techniques include removing disc material which separates the vertebrae and impacting bone into the disc area. The impacted bone fuses with the bone material of the vertebrae to thereby fuse the two vertebrae together. In a further advance in the art, spinal implants have been developed to increase the probability of a successful fusion. An example of such a spinal implant is shown in U.S. Pat. No. 5,489,308, which shows a threaded spinal implant which includes a hollow cylinder into which bone chips or bone slurry may be placed. The cylinder has holes extending radially therethrough. The bone material grows through the holes to fuse with the bone material of the vertebrae. Similar threaded spinal implants are disclosed in U.S. Pat. Nos. 5,489,307; 5,263,953; 5,458,638; and 5,026,373; the disclosures of all of the foregoing patents are incorporated herein by reference.

The metallic surfaces of these spinal implants, other than the threaded structure with large pores, is essentially smooth without pillars, micropillars or surface texturing. Without such surface texturing the spinal implants in some circumstances may not mechanically anchor at an early date or affix into the adjoining bone as much as is desirable, and may not effectively minimize fibrous capsule formation around the implant. There is a need for a spinal implant with pillars, micropillars, fins or surface texturing which addresses these problems and provides improvements in these areas; the present invention is such an implant.

SUMMARY OF THE INVENTION

A spinal implant comprising a hollow, generally tubular shell having an exterior lateral surface, a first end and a second end. The shell has a helical thread projecting from its exterior surface, the thread comprising a plurality of pillars. Each pillar has a height of 100–4500 microns and a lateral dimension at the widest point of 100–4500 microns. The exterior surface has a plurality of holes therethrough to permit bone growth therethrough. Alternatively, a plurality of pillars may project from the exterior surface of the shell in a regular, non-helical array.

BRIEF DESCRIPTION OF THE DRAWINGS

FIG. 1 is a side elevational view of a spinal implant according to the invention.

FIG. 2 is a cross-sectional view taken along line 2—2 of FIG. 1.

FIG. 3 is a plan view of a portion of the outer surface of the implant of FIG. 1.

FIG. 4 is a cross-sectional view taken along line 4—4 of FIG. 3.

FIG. 5 is a plan view of an alternative embodiment of the surface of FIG. 3.

FIG. 6 is a cross-sectional view taken along line 6—6 of FIG. 5.

FIG. 11A is a plan view similar to FIG. 5 with the top half of each pillar removed showing an alternative embodiment.

FIG. 12 is a plan view similar to FIG. 5 showing an alternative embodiment.

FIG. 13 is a plan view similar to FIG. 12 showing an alternative embodiment.

FIG. 14 is a plan view similar to FIG. 13 showing an alternative embodiment.

FIG. 15 is a plan view similar to FIG. 13 showing an alternative embodiment.

FIG. 16 is a plan view similar to FIG. 15 showing an alternative embodiment.

FIG. 17 is a plan view similar to FIGS. 5 and 12 showing an alternative embodiment.

FIG. 18 is a plan view similar to FIG. 17 showing an alternative embodiment.

FIG. 19 is a plan view similar to FIG. 18 showing an alternative embodiment.

FIG. 20 is a plan view similar to FIG. 17 showing an alternative embodiment.

FIG. 21 is a plan view similar to FIG. 20 showing an alternative embodiment.

FIG. 22 is a plan view of an alternative embodiment of a pillar or fin.

DETAILED DESCRIPTION OF THE PREFERRED EMBODIMENTS OF THE INVENTION

Figures 23, 24:
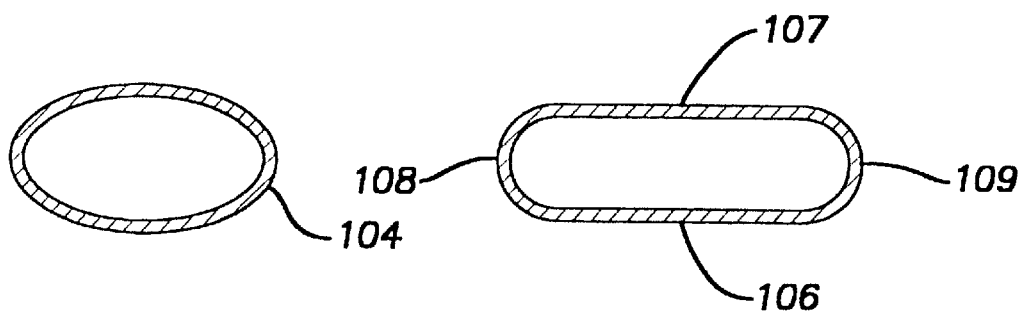
FIG. 23 is a cross-sectional view of an alternative embodiment of the implant of FIG. 1.
FIG. 24 is a cross-sectional view of an alternative embodiment of the implant of FIG. 1.

Generally, the same number is used to identify the same element which appears in different Figures. With reference to FIGS. 1–2, there is shown a spinal implant 10 of a conventional material such as titanium or other metal or metal alloy having threads or thread segments 12; the spinal implant 10 preferably has only one thread which spirals helically around the implant approximately eight times, a single spiral or helical thread at twelve threads per inch being known in the art. Thread 12 spirals helically around the implant 10 in the conventional manner, less preferably a plurality of intertwined helical threads may be provided. Spaces or valleys 15 are provided between the threads; preferably, as known in the art, there is only a single valley 15 which spirals helically around the implant approximately eight times and which is defined by the turns of the helical thread. Less preferably the valley 15 can be flat across instead of trough-shaped, so that there is no dip, so that a flat surface joins the base surface 32 of one thread with the base surface 32 of the adjacent thread. A terminal portion 14 of the thread is shown at one end of the implant. The implant 10 includes a hollow, generally tubular, preferably generally cylindrical shell as shown in FIGS. 1–2 and has an exterior lateral surface having a helical thread 12 projecting therefrom as shown in FIG. 1. The cross-section of the cylindrical shell of the implant 10 is preferably circular as known in the art; less preferably it is oval as shown in FIG. 23, less preferably rectangular or rectangular with rounded ends as shown in FIG. 24 (like a squashed oval). The implant 10 has a leading or first end 7 and a trailing or second end 8; the helical nature of thread 12 permits thread 12 to engage vertebra material as the implant is screwed in (with leading end 7 leading the way) and draw the implant into the spine. The implant has a longitudinal axis down the center of the cylinder and the thread 12 is helically oriented around this axis.

As known in the art, a spinal implant is generally a hollow threaded cylinder made of a titanium alloy, about 12–18 mm in diameter and 20–28 mm in length. Polyethylene or plastic caps may be used on the ends of the implant to maintain the cage material inside. Inside the cylindrical spinal implant 10 is a first interior chamber 16, a second interior chamber 18, and reinforcing ribs 20, 24, 26. Holes 22 are provided radially through the side surface of the implant to permit bone growth therethrough. Larger holes than those shown in FIG. 1 may also be provided, as is known in the art (see U.S. Pat. No. 5,489,307, incorporated herein by reference). The threads 12 comprise a plurality of pillars or micropillars 6. Preferably the entirety of thread 12 or all the turns of thread 12 comprises pillars, less preferably at least 75%, 50%, or 25% of thread 12 comprises pillars. Pillars as used in the claims herein includes cylindrical pillars, square pillars, rectangular pillars, and crescent-shaped pillars.

With reference to FIGS. 3–4, there is shown a detail of the surface of the implant 10 showing pillars 6 extending from base surface 32 of the thread 12, the threads being separated by valleys 15. Each pillar 6 in FIGS. 3–4 is essentially an inverted truncated cone, each pillar 6 having a truncated cone side surface 28 and a round top face 30. As shown in FIG. 4, the side surface 28 of pillar 6 is undercut, having an undercut angle A—A which is preferably 10°–20°.

With reference to FIGS. 5–6, there is shown an alternative embodiment comprising square four-sided truncated pyramidal pillars 34 extending from base surface 32 between valleys 15, each pillar 34 being undercut by an angle C—C of preferably 10°–20° on all four faces to yield side surface face 36, the pillar having a square top face 38. The base surface 32 is typically about 900 microns wide.

Figure 7:
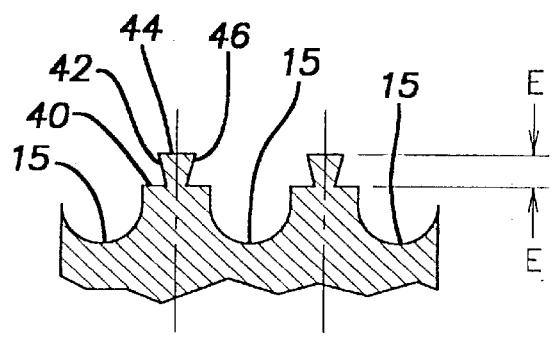
FIG. 7 is a cross-sectional view similar to FIG. 6 showing an alternative embodiment.

With reference to FIG. 7, there is shown an alternative embodiment wherein pillars 46, which may be cylindrical or square as described above, extend from base surface 40, have a top face 44 and are undercut as described above yielding side surface 42.

Figure 8:
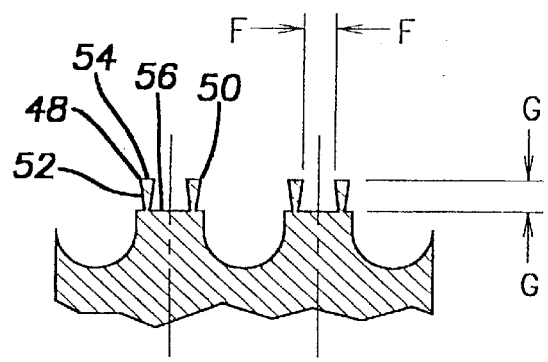
FIG. 8 is a cross-sectional view similar to FIG. 7 showing an alternative embodiment.

With reference to FIG. 8, there is shown an alternative embodiment similar to FIG. 7, but wherein each pillar in FIG. 7 is replaced by a pair of pillars in FIG. 8; pillars 48, 50 extending from base surface 56 are the same and are side by side (alternatively they are staggered), each pillar being square or circular in top view, having a top face 54 and being undercut as described above to yield side surface 52. As shown in FIG. 8, the pair of pillars 48, 50 define a line which is laterally oriented with respect to the direction of the thread, that is, the helical line defined by the helical thread.

Figure 9:
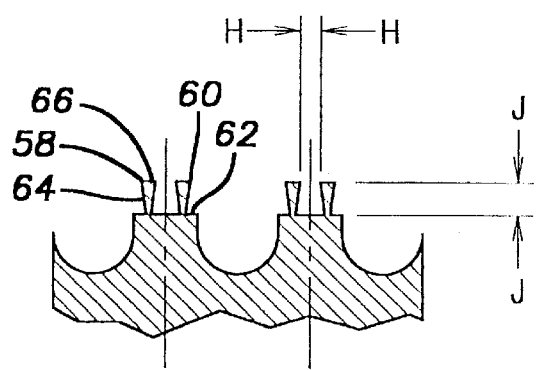
FIG. 9 is a cross-sectional view similar to FIG. 8 showing an alternative embodiment.

FIG. 9 is an alternative embodiment similar to FIG. 8, wherein pillars 58, 60, which are circular or square in top view and are the same and are side by side, extend from base surface 62, have a top surface 66, and are undercut as described above to yield a side surface 64.

Figure 10:
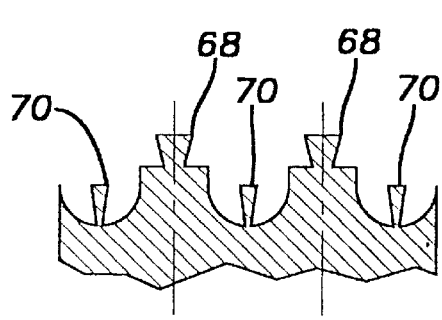
FIG. 10 is a cross-sectional view similar to FIG. 7 showing an alternative embodiment.
Figure 11:
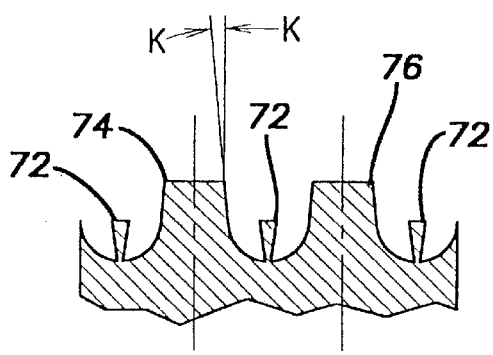
FIG. 11 is a cross-sectional view similar to FIG. 10 showing an alternative embodiment.

FIG. 10 shows an alternative embodiment identical to FIG. 7, except that a pillar 70 is placed in each valley adjacent each pillar 68; each pillar 70 having the same dimensions as pillar 48. FIG. 11 shows an alternative embodiment similar to FIG. 10, wherein pillars 72 are the same as pillars 70, but the threads 74, 76 are solid without pillars, thus having the appearance of a conventional thread, and having a sloping side surface having an angle of about 5°, less preferably 1°–10°, as shown at K—K.

FIG. 12 is a plan view similar to FIG. 5 showing an alternative embodiment wherein regularly-arrayed pillars or fins 78 are rectangular in top view and extend from base surface 79 to form threads which are separated by valleys 15. Alternatively, every other pillar 78 can be rotated 90° so it is oriented laterally rather than longitudinally. FIG. 13 is an alternative embodiment similar to FIG. 12, except that regularly-arrayed rectangular pillars 80 extending from base surface 81 are oriented laterally rather than longitudinally. FIG. 14 is an alternative embodiment similar to FIG. 13, except that each pillar 82 extending from base surface 83 is staggered between the pillars in the adjacent threads, rather than being directly across from the pillars in the adjacent threads.

FIG. 15 shows an alternative embodiment similar to FIG. 13, wherein each pillar 84a, 84b, and 84c extending from base surface 85 is angled with respect to the longitudinal axis of the thread on which it is placed, the angle being preferably 45°, less preferably 30°–60°, angled having the conventional meaning of other than 0°, 90° and 180°. As helical thread 12 progresses helically around implant 10, it travels 360° each time or turn around the implant. As shown in FIG. 15, every 360° or one turn around the implant, the angle of the pillars is rotated 90° as shown in FIG. 15 so that the angle of the pillars alternates in adjacent threads to yield a herringbone arrangement as shown in FIG. 15. Holes 71a, 71b are provided in valleys 15a, 15c to permit bone chip placement or deposit therethrough as described below, and subsequent bone growth therethrough. Since the implant is screwed into position in the spine of the patient, each fin or pillar acts like a tiny snowplow blade pushing snow to the side of the street; that is, as the implant is screwed in, each fin shaves additional bone from the adjacent bony tissue and pushed it in a certain direction. If the implant segment shown in FIG. 15 is raked downwardly (corresponding to the implant being screwed in), fins 84a will shave off bone chips or fragments and push them toward holes 71a; fins 84b will shave off bone fragments and push them in the opposite direction toward holes 71b; fins 84c will shave off bone fragments and also push them toward holes 71b. Thus the holes are placed in every other valley, not every valley, the holes being placed in the valleys where the bone fragments are being pushed. Note valleys 15b and 15d do not have holes and the alternate valleys 15a and 15c do have holes. The fins may be tilted toward the holes or undercut more severely or with a concave surface on the side or portion facing the holes to assist in pushing the bone fragments down toward the holes. In this way additional bony material is driven down into the holes and into the implant as it is screwed in, or at least driven toward or adjacent the holes to facilitate bone growth through the holes. These concepts are further illustrated by FIG. 22, where a scalloped or crescent-shaped pillar or fin 100 having ends 101 and 102 is shown in top view. These fins 100 can be substituted for the fins in FIG. 15 and oriented on an angle so as to scrape or shave off bone fragments and direct or push them towards the holes 71a, 71b. The ends 101, 102 can alternatively be flat, have a blunt point, or have a small or large radius of curvature. To be more effective, these fins for scraping may be spaced further apart and placed in particular at the leading end 7 of the implant 10. With regard to the herringbone arrangement in FIG. 15, alternatively the angle of the pillars may be kept constant all over the implant and not rotated periodically to form the herringbone arrangement. The pillars can be staggered or un-staggered with respect to the pillars in adjacent threads. Alternatively the holes may be placed in all the valleys or staggered or eliminated.

FIG. 16 shows an alternative embodiment similar to FIG. 15, except that each pillar 86 extending from base surface 87 is rotated 90° from the orientation of the immediately preceding pillar in the thread. The pillars 86 can be staggered or un-staggered with respect to the pillars in adjacent threads.

Any combinations of any of the arrangements described herein can also be provided.

Figure 8A:
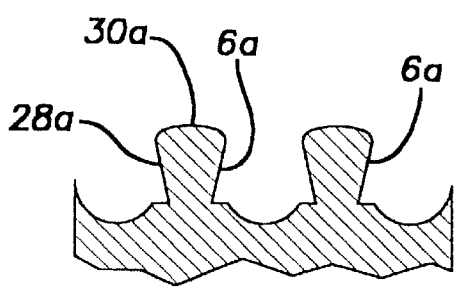
FIG. 8A is a cross-sectional view similar to FIG. 4 showing an alternative embodiment.

The pillars preferably or alternatively have a top face which is somewhat rounded instead of flat and without sharp edges which may have a potential for tissue necrosis. This can be achieved by sandblasting the pillars after fabrication or treating them chemically to take the edges off. This embodiment is illustrated in FIG. 8A, which is the same as FIG. 4, except that each pillar 6a has a top face 30a which is somewhat rounded and the sharp edge where top face 30a meets side surface 28a has been removed, these changes being achieved by sandblasting or chemical treatment. This feature is further illustrated in FIG. 11A, which is the same as FIG. 5, except that the top half of each pillar 34 has been removed to show cutaway top surface 38a and to illustrate that each of the four side edges 39 of the pillar 34 has been rounded (such as replaced by a radius of curvature) and the sharp edge removed such as by sandblasting or chemical treatment. Furthermore a radius of curvature or fillet can be provided at or around the base of each pillar where it joins or attaches to the surface.

In the Figures, dimension B—B in FIG. 4 is preferably 1000 microns and the following dimensions are preferably the following lengths: D—D—1000 microns; E—E—500 microns; G—G—500 microns; J—J—500 microns. Height is measured from the base surface to the top face, width is measured at the top face (width of a circle being the diameter), and the edge-to-edge distance is measured at the top face. In FIG. 8 the edge-to-edge distance F—F is preferably 500 microns and in FIG. 9 the edge-to-edge distance H—H is preferably 250 microns. In FIGS. 3–6, the pillars are preferably 1000 microns in width; in FIG. 7 the pillars are 500 microns in width, and in FIGS. 8–9 the individual pillars are 250 microns in width. The angles A—A and C—C are preferably 10°–20°, less preferably 5°–30°. Less preferably these angles may be 0°. Alternatively, the pillars may be wider at the bottom than at the top, so that the side surfaces slope outward as they get closer to the base, by an amount such as 1°–30°, more preferably 1°–10°, more preferably 1°–5°. The valleys 15 are typically 250–3000, more preferably 500–2000, more preferably about 1000, microns wide.

The pillars on the external surface of the spinal implant will help to more effectively mechanically anchor the implant at an early date and affix the implant into the adjoining bone and more effectively reduce, minimize or disrupt fibrous capsule formation around the implant.

The pillars of the implant are preferably inverted truncated cones or pyramids as illustrated, preferably with the above dimensions. In FIGS. 12–16, the pillars or fins have a rectangular top face having a width of 100–1000, more preferably 200–950, more preferably 300–900, more preferably 400–825, more preferably 500–750, less preferably about 250, less preferably 200–250, less preferably 150–300, microns and a length of 400–4500, more preferably 500–3000, more preferably 600–2000, more preferably 700–1750, more preferably 1000–1500, microns (the length being greater than the width and preferably being 2–10, more preferably 2–6, more preferably 2–4, times the width); otherwise these pillars are dimensionally the same as the pillars described above.

Less preferably the dimensions or distances of the pillars mentioned herein can be within a range ±5%, less preferably ±10%, less preferably ±20%, less preferably ±30%, less preferably ±40%, less preferably ±50%.

The height of the pillars is preferably 100–4500 microns, more preferably 100–2500 microns, more preferably 150–2000 microns, more preferably 200–1500 microns, more preferably 400–1200 microns, more preferably 500–1000 microns, alternatively about 500 or 1000 microns. The width of the pillars is preferably 100–4500, more preferably 100–3000, more preferably 150–2000, more preferably 200–1500, more preferably 250–1000, microns. Where a pair of pillars is on the same thread as in FIG. 8, the edge-to-edge distance is preferably 100–3000, more preferably 100–2000, more preferably 130–1000, more preferably 160–800, more preferably 200–600, more preferably 250–500, microns. The lateral dimension at the widest point of each pillar (for circular and square pillars the width and for rectangular pillars the length) is preferably 100–4500, more preferably 150–2500, more preferably 200–1500, microns.

Two adjacent pillars in the same thread (i.e., without crossing a valley) such as in FIGS. 1, 18 and 19 have an edge-to-edge distance preferably the same as the width of the pillar or alternatively 100–4500, more preferably 100–2000, more preferably 250–1000, microns or 250, 500 or 1000 microns. For fins or rectangular pillars such as in FIGS. 12–16, the edge-to-edge distance is preferably about the width of the pillar, or 100–4500, more preferably 100–2500, more preferably 250–1000, microns, or as shown in FIGS. 12–16, or 250, 500, or 1000 microns.

Less preferably pillars such as those described above can be placed on the interior surface of the implant (to help hold the bone in place), but preferably without undercutting.

The metal surfaces of the implant can optionally be coated with hydroxy appetite, bone morphogenic protein, or other bone inductive agents.

Conventional spinal implants are provided with large holes, such as at 22 in FIGS. 1–2, for bone growth therethrough. The present invention also provides a plurality of smaller, more effective holes for bone growth therethrough. FIG. 17 is an alternative embodiment similar to FIGS. 5 and 12 showing valleys 15, pillars 88 extending from the base surface 32, and holes 90 provided between the pillars 88. FIG. 18 is an alternative embodiment similar to FIG. 17 showing pillars 91 in the threads and holes 92 in the valleys 15. FIG. 19 is an alternative embodiment similar to FIG. 18 showing pillars 93 in the threads and fin holes or rectangular holes 94 in the valleys 15. FIG. 20 is an alternative embodiment wherein the cylindrical surface of the spinal implant 10 has a smooth unthreaded surface 95 from which the pillars 96, which are regularly-arrayed and non-helical, directly emerge, and has holes 97 between the pillars 96. FIG. 21 is an alternative embodiment similar to FIG. 20, also having a smooth unthreaded surface 89 from which fins or rectangular pillars 98, which are arrayed in a non-helical herringbone arrangement or herringbone type pattern, directly emerge, interspersed with holes 99.

With reference to FIGS. 17–21, the pillars may be any of the pillars described herein. The round holes go through the wall of the implant into the interior chamber and are preferably 150–1500, more preferably 200–1250, more preferably 250–1000, alternatively 375–750, alternatively 450–575, alternatively about 500, microns in diameter, with 250, 500, and 1000 microns being typical hole diameters. The rectangular holes 94 have the same width and length dimensions as the width and length dimensions of the pillars or fins in FIGS. 12–16. Rectangular holes may be substituted for round holes and vice versa. Rectangular holes may be oriented longitudinally or laterally or at an angle or a combination thereof, such as alternating longitudinal and lateral, or oriented as the fins in FIGS. 12–16 are oriented. The holes may be staggered or unstaggered with respect to each other and with respect to the pillars. The pillars may be staggered or unstaggered with respect to each other and with respect to the holes. Any of the foregoing arrangements may be combined on the same implant, such as the holes in FIGS. 17 and 18 being placed into the same implant.

Although the preferred embodiments of the invention have been shown and described, it should be understood that various modifications may be resorted to without departing from the scope of the invention as disclosed and claimed herein.

What is claimed is:

1. A spinal implant comprising a hollow, generally tubular shell having an exterior surface, a first end, and a second end, said shell having a helical thread projecting from said exterior surface, said thread comprising a plurality of pillars, each pillar having a height of between about 100–4500 microns and a dimension in a direction perpendicular to the height of between about 100–4500 microns, so as to facilitate bone ingrowth and mechanical anchoring of said spinal implant and to discourage formation of a fibrous capsule around said spinal implant, said exterior surface having a plurality of holes therethrough to permit bone growth therethrough.

2. A spinal implant according to claim 1, each pillar being substantially square in top view and having a height of 150–2000 microns, a width of 200–1500 microns, and at least some adjacent pillars having an edge-to-edge distance of 100–4500 microns.

3. A spinal implant according to claim 1, each pillar being substantially rectangular in top view and having a width of 100–1000 microns and a length of 400–4500 microns and a height of 150–2000 microns, and adjacent pillars in the same thread having an edge-to-edge distance of 100–4500 microns.

4. A spinal implant according to claim 1, a plurality of said pillars having a side surface which is undercut at an undercut angle of 5°–30°.

5. A spinal implant according to claim 1, said thread comprising a plurality of pairs of pillars, each pair of pillars being two pillars which are side-by-side, each pair defining a line which is laterally oriented with respect to the direction of the thread.

6. A spinal implant according to claim 1, each pillar being substantially without sharp edges.

7. A spinal implant according to claim 1, said helical thread defining a helical valley between turns of said thread, a plurality of pillars projecting from said valley.

8. A spinal implant according to claim 3, wherein at least some of said rectangular pillars are arranged in pairs, each pair of rectangular pillars being two pillars which are side-by-side, each pair defining a line which is laterally oriented with respect to the direction of the thread.

9. A spinal implant according to claim 3, wherein said thread has a longitudinal axis, and wherein at least some of said rectangular pillars are angled with respect to said longitudinal axis of said thread.

10. A spinal implant according to claim 3, wherein said thread has a longitudinal axis, and wherein said rectangular pillars are disposed at angles with respect to said longitudinal axis of said thread, said angles alternating in adjacent threads such that the rectangular pillars in adjacent turns of the thread form a herringbone arrangement.

11. A spinal implant according to claim 10, said helical thread defining a helical valley between turns of said thread, a plurality of holes being provided in said valley through said shell.

12. A spinal implant according to claim 1, a hole through said shell being provided between a pair of said pillars which are adjacent one another in said thread.

13. A spinal implant according to claim 1, said helical thread defining a helical valley between turns of said thread, a plurality of holes being provided in said valley through said shell.

14. A spinal implant according to claim 1, said implant being coated with bone inductive agent.

15. A spinal implant according to claim 1, wherein each of said pillars has an outer planar surface.

* * * * *